United States Patent [19]

Lueschen et al.

[11] Patent Number: 5,449,291
[45] Date of Patent: Sep. 12, 1995

[54] DENTAL IMPLANT ASSEMBLY HAVING TACTILE FEEDBACK

[75] Inventors: Jeffrey D. Lueschen; Brooks J. Story, both of Carlsbad, Calif.

[73] Assignee: Calcitek, Inc., Carlsbad, Calif.

[21] Appl. No.: 171,566

[22] Filed: Dec. 21, 1993

[51] Int. Cl.$^6$ .............................................. A61C 8/00
[52] U.S. Cl. .................... 433/173; 433/172; 433/174
[58] Field of Search ............... 433/172, 173, 174, 175, 433/176, 177, 178

[56] References Cited

U.S. PATENT DOCUMENTS

| | | | |
|---|---|---|---|
| 3,979,828 | 9/1976 | Taylor | 32/10 A |
| 4,756,691 | 7/1988 | Pilarek | 433/177 |
| 4,854,872 | 8/1989 | Detsch | 433/174 X |
| 4,976,739 | 12/1990 | Duthie, Jr. | 623/16 |
| 5,125,840 | 6/1992 | Durr et al. | 433/173 |
| 5,195,892 | 3/1993 | Gersberg | 433/173 X |
| 5,213,500 | 5/1993 | Salazar et al. | 433/173 X |
| 5,302,126 | 4/1994 | Wimmer et al. | 433/173 |

FOREIGN PATENT DOCUMENTS 3300764 7/1984 Germany ........................... 433/173

OTHER PUBLICATIONS

Hotz, W., "Surgical Instructions for Two-Phase Tiolox-Screws," pp. 1-12, Feb. 1992, Germany.
Hotz, W., "The Tiolox Implant System," Zahnarztliche Praxis, vol. 7, pp. 254-256, No. 42, Jul. 12, 1991, Germany.

Primary Examiner—Nicholas D. Lucchesi
Attorney, Agent, or Firm—Richard L. Robinson

[57] ABSTRACT

A dental implant assembly includes an implant for osseointegration in alveolar bone, an abutment removably attached to the implant for supporting a tooth prosthesis, and a screw received through an axial bore in the abutment and engaging a threaded bore in the implant. The implant includes an annular shoulder and a plurality of splines spaced from one another to define slots therebetween and disposed circumferentially about the opening of the threaded bore. The abutment includes an annular end face in engagement with the annular shoulder of the implant. A cylindrical recess is disposed radially inwardly of the annular end face and receives the splines of the implant therewithin. The cylindrical recess communicates with the axial bore. A plurality of circumferentially spaced axially extending splines defining slots therebetween are disposed within the cylindrical recess and are interleaved with the splines of the implant. The end faces of the splines of the abutment are recessed axially from the annular end face by an amount less than one half the axial length of the splines of the abutment to provide piloting of the splines of the implant in the cylindrical recess without generating ambiguous tactile feedback that would erroneously indicate full seating of the splines prior to the splines being rotated into full alignment.

12 Claims, 2 Drawing Sheets

DENTAL IMPLANT ASSEMBLY HAVING TACTILE FEEDBACK

BACKGROUND OF THE INVENTION

1. Field of the Invention

The present invention relates generally to dental implants, and more particularly to a dental implant assembly of the type having an implant portion for osseointegration in alveolar bone and an abutment portion securable to the implant portion for supporting a dental prosthesis.

2. Background Information

One known arrangement for a dental implant involves an implant portion, or artificial root, that is received in a hole prepared in alveolar bone, and an abutment, or prosthesis support, that is securable to the implant portion and that extends beyond the gingival tissue to support a tooth prosthesis. The implant portion and the abutment are constructed as separate components that are secured together by means of a screw passed through the abutment and received within a threaded bore in the implant portion.

In a first surgical procedure, an incision is made in the gingival tissue to expose the alveolar bone. Following any dressing of the surface of the bone that may be necessary, a hole that is complementary in shape to the implant portion is drilled in the bone and the implant portion is inserted. A healing cap or screw is attached to the implant portion to occlude the threaded bore, and the gingival tissue is stitched closed over the implant portion to await osseointegration.

In a subsequent second operation, following osseointegration of the implant portion, the gingival tissue is again opened to expose the implant portion. The healing cap or screw is removed and replaced with a second healing cap having an outer surface corresponding in shape below the gumline to that of the abutment, but protruding slightly above the gingival tissue. The gingival tissue surrounding the second healing cap is sutured thereabout to await healing in conformity to the outer surface of the second healing cap. After the gingival tissue has healed, the second healing cap is removed and replaced with a permanent abutment supporting a tooth prosthesis fashioned thereon.

In addition to providing a screw to secure the abutment to the implant portion, it is also known to configure the interface between the abutment and implant portion to resist rotation of the abutment relative to the implant portion. One such configuration involves a raised hexagon protruding from the abutment-engaging end of the implant portion that is received in a complementary hexagonal recess in the implant-engaging end of the abutment. Alternatively, it is known to provide the hexagonal recess in the implant and the raised hexagon on the abutment. Such arrangements not only provide resistance to rotation, but provide for indexing of the abutment in a plurality of angular orientations relative to the implant.

Another anti-rotation configuration is illustrated in U.S. Pat. No. 5,125,840 to Dürr et al., issued Jun. 30, 1992, which shows a base body for implantation in bone that is provided with a threaded internal bore. In the upper end, a recess is formed that is of a larger diameter than the threaded bore to provide a stop shoulder at the junction of the recess and threaded bore. The stop shoulder is provided with four circumferentially spaced pockets. A ring member, or abutment, is provided with a centering collar having an external diameter that corresponds to the diameter of the recess of the base body. The centering collar has four circumferentially spaced tongues which are complementary to the interlocking pockets of the base body and coact therewith to prevent twisting between the ring member and the base body. A screw is received through the ring member and threadedly received in the threaded bore of the base body to secure the ring member to the base body.

One factor that is considered important by those persons who implant dental implants is the tactile feedback that is provided as the abutment is seated on the implant portion. During assembly of the abutment to the implant, it is important that tactile feedback be provided to positively indicate that the abutment is fully seated on the implant before the securing screw is tightened. Where anti-rotation features that permit indexing are provided, it is also useful to provide for piloting of the abutment on the implant to assist in aligning the abutment axially with the implant prior to seating the indexing features.

The complementary hexagon arrangement provides positive indication of seating in that the abutment moves suddenly in the axial direction through the full length of engagement of the hexagonal surfaces as the complementary surfaces become aligned. There is, however, no piloting of the abutment relative to the implant prior to complete alignment of the hexagons, and thus no assistance is provided to maintain the abutment and implant in axial alignment as the abutment is rotated to align the hexagons.

The arrangement shown in Dürr provides for piloting of the abutment relative to the implant since the centering collar of the ring member is received in the recess of the base member prior to the tongues of the ring member engaging the pockets of the base body. However, due to the depth of the recess, the ring member travels more than half its ultimate length of engagement with the base body before the tongues and pockets even begin to engage. Thus, it is possible that the initial axial displacement could be mistaken for complete seating of the ring member relative to the base member, without the tongues and pockets having engaged.

SUMMARY OF THE INVENTION

In accordance with one aspect of the invention, a dental implant assembly involves an implant for osseointegration in alveolar bone. The implant includes an elongate body having a proximal end and a distal end, an axial threaded bore open at the distal end, an annular shoulder at the distal end, and a plurality of splines spaced from one another to define slots therebetween and disposed circumferentially about the opening of the threaded bore at the distal end and extending axially away from the shoulder. Each of the splines has a curved outer wall lying on a common circle disposed radially inwardly of the shoulder. An abutment is removably attached to the implant for supporting a tooth prosthesis. The abutment includes a proximal end and a distal end and an annular end face at the proximal end of the abutment in engagement with the annular shoulder of the implant. The abutment also includes an axial bore having an internal shoulder, a cylindrical recess disposed radially inwardly of the annular end face and receiving the splines of the implant therewithin. The cylindrical recess communicates with the axial bore, and a plurality of circumferentially spaced axially extending splines defining slots therebetween are disposed within the cylindrical recess. Each of the splines of the abutment are received in a respective slot of the implant between adjacent splines of the implant, and each of the slots of the abutment receive a respective spline of the implant between adjacent splines of the abutment. The splines of the abutment have proximal end faces and have an axial length. The proximal end faces are recessed axially from the annular end face by an amount less than one half the axial length of the splines of the abutment. A screw is received in the axial bore of the abutment and has a head engaging the interior shoulder of the axial bore and has screw threads threadedly engaged with the threaded bore of the implant.

It is an object of the present invention to provide a dental implant assembly including an implant portion and an abutment, wherein the abutment resists rotation relative to the implant and is indexable relative thereto, and wherein the abutment is pilotable on the implant prior to full engagement with the implant, and yet provides a positive tactile feedback indicative of full engagement.

Other objects and advantages of the present invention will be apparent from the following description of a preferred embodiment made with reference to the drawings.

DETAILED DESCRIPTION OF THE PREFERRED EMBODIMENTS

Figure 2:
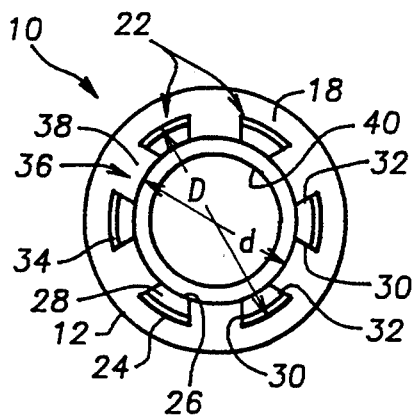
FIG. 2 is an end view of the implant of FIG. 1 viewing the abutment-engaging end of the implant.
Figure 1:
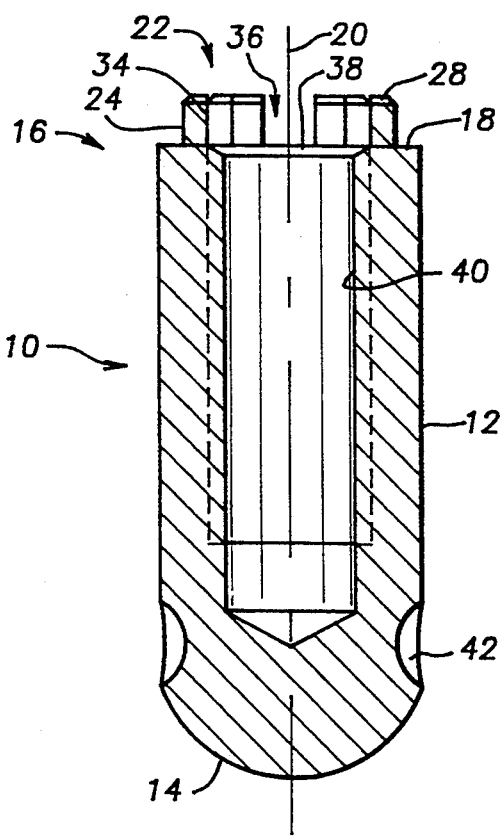
FIG. 1 is a cross-section of an implant useful for osseointegration within alveolar bone taken along a plane including the longitudinal axis of the implant.

Referring to FIGS. 1 and 2, there is illustrated an implant 10 comprising part of a dental implant assembly and configured in accordance with the present invention. Implant 10 is preferably constructed of a biocompatible material such as titanium that is coated with hydroxyapatite to further promote osseointegration. Implant 10 includes an elongate cylindrical body 12 having a proximal end 14 and a distal end 16. As used throughout this description, the term proximal refers to that end or direction that is toward alveolar bone when the dental implant assembly is implanted, and the term distal refers to that end or direction that is away from alveolar bone and toward the oral cavity when the dental implant assembly is implanted. Proximal end 14 is smoothly rounded and approximately hemispherical. Distal end 16, which may also be referred to as the abutment-engaging end for reasons that will shortly become apparent, includes an annular shoulder 18 that extends to the periphery of cylindrical body 12 and lies in a plane perpendicular to the longitudinal axis 20 of cylindrical body 12.

A plurality of splines 22 rise from and extend axially away from shoulder 18 in the distal direction. Each spline 22 is defined by an outer surface 24, an inner surface 26, an end face 28 and side surfaces 30 and 32. An annular chamfer 34 connects outer surface 24 and end face 28. Outer surface 24 is a curved surface comprising an arc portion of a cylindrical surface having a diameter D and lying parallel to the longitudinal axis 20 of cylindrical body 12. Diameter D is less than the diameter of cylindrical body 12, with one-half the difference representing the radial width of annular shoulder 18. Each outer surface 24 of each one of the plurality of splines 22 lies on a common circle having a diameter D and centered on longitudinal axis 20. Inner surface 26 is a curved surface comprising an arc portion of a cylindrical surface having a diameter d and lying parallel to the longitudinal axis 20 of cylindrical body 12. Diameter d is less than diameter D, with one-half the difference representing the radial width of each spline 22. Each inner surface 26 of each one of the plurality of splines 22 lies on a common circle having a diameter d and centered on longitudinal axis 20. Side surfaces 30 and 32 are each defined by planes that lie parallel to longitudinal axis 20 and parallel to, but displaced from, a respective diameter of cylindrical body 12. Each of the plurality of splines 22, of which there are preferably six, is uniformly dimensioned and uniformly circumferentially spaced about distal end 16 of implant 10. Thus, adjacent side surfaces 30 and 32 of next adjacent splines 22 are parallel to one another and each side surface 30 or 32 is co-planar with a corresponding side surface of a generally oppositely disposed spline. Adjacent side surfaces 30 and 32 of next adjacent splines 22 can be considered as defining the side walls of a diametrically oriented slot 36 therebetween. Each slot 36 extends in the distal axial direction the full axial length of splines 22. Consequently, each slot 36 has a bottom surface 38 that is coplanar with annular shoulder 18.

A central coaxial threaded bore 40 in cylindrical body 12 is open at distal end 16 and has a major diameter equal to diameter d. Four uniformly circumferentially spaced round depressions 42 are disposed in the outer surface of implant 10 at the junction of cylindrical body 12 and rounded proximal end 14. Depressions 42 receive bone ingrowth to assist in anchoring implant 10 in the alveolar bone.

Figure 3:
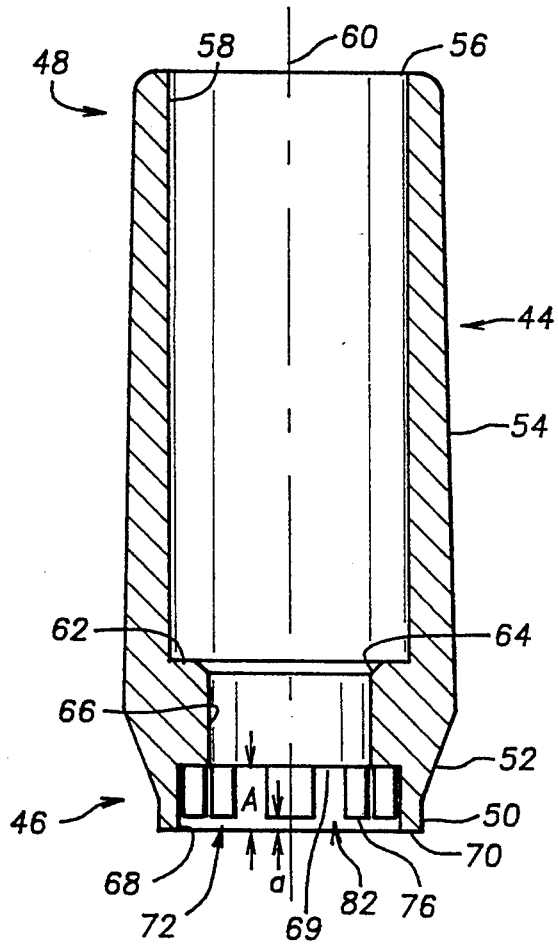
FIG. 3 is a cross-section of an abutment useful in combination with the implant of FIG. 1 taken along a plane including the longitudinal axis of the abutment.
Figure 4:
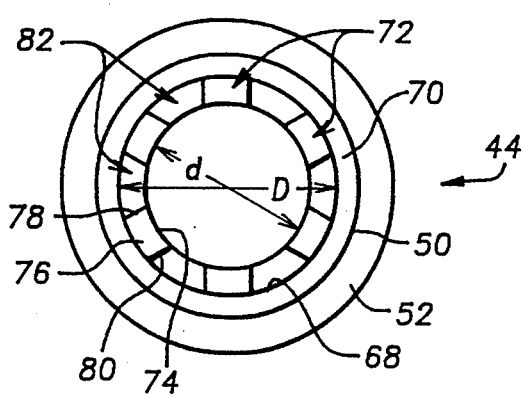
FIG. 4 is an end view of the abutment of FIG. 3 viewing the implant-engaging end of the abutment.

Referring to FIGS. 3 and 4, there is illustrated an abutment 44 configured in accordance with the present invention and particularly configured to mate with the implant 10 illustrated in FIGS. 1 and 2. Abutment 44 is preferably constructed of a biocompatible material such as titanium. Abutment 44 includes a proximal, or implant-engaging, end 46 and a distal end 48. Starting at proximal end 46, the outer surface of abutment 44 is defined by a cylindrical surface 50 followed by a frustoconical surface 52 that tapers radially outwardly in the distal direction, followed by a frustoconical surface 54 that tapers radially inwardly in the distal direction. The outer surface of abutment 44 terminates at distal end 48 at a distal annular end face 56. A cylindrical bore 58 is open at distal end 48 and extends coaxially with the longitudinal axis 60 to an internal annular shoulder 62, which is connected via an annular chamfer 64 to a cylindrical bore 66 of lesser diameter than cylindrical bore 58. A cylindrical recess 68 having a diameter D and a depth A defined by a bottom wall 69 and coaxially aligned with longitudinal axis 60 is provided in proximal end 46.

Cylindrical recess 68 communicates with cylindrical bore 66 which in turn communicates with cylindrical bore 58. A proximal annular end face 70 lying in a plane perpendicular to longitudinal axis 60 is defined between outer cylindrical surface 50 and recess 68. A plurality of splines 72 extend axially from bottom wall 69 of recess 68 in the proximal direction and extend radially inwardly from cylindrical recess 68. Each spline 72 is additionally defined by an inner surface 74, an end face 76 and side surfaces 78 and 80. Inner surface 74 is a curved surface comprising an arc portion of a cylindrical surface having a diameter d and lying parallel to the longitudinal axis 60 of abutment 44. Diameter d is less than diameter D, with one-half the difference representing the radial width of each spline 72. Each inner surface 74 of each one of the plurality of splines 72 lies on a common circle having a diameter d and centered on longitudinal axis 60. Side surfaces 78 and 80 are each defined by planes that lie parallel to each other and to longitudinal axis 60, and lie parallel to and on opposite sides of a line drawn diametrically across abutment 44. Each of the plurality of splines 72, of which there are preferably six, is uniformly dimensioned and uniformly circumferentially spaced about proximal end 46 of abutment 44. Thus, adjacent side surfaces 78 and 80 of next adjacent splines 72 are disposed obliquely to one another and tend toward convergence in the radially inward direction. Adjacent side surfaces 78 and 80 of next adjacent splines 72 can be considered as defining the side walls of a slot 82 therebetween. Each slot 82 extends in the distal axial direction the full axial length of splines 72. Consequently, each slot 82 has a bottom surface defined by bottom surface 69 of recess 68. Each spline 72 has an axial length that is somewhat less than the depth A of recess 68. The difference "a" is the amount by which the proximal end faces 76 of each spline 72 are recessed from the plane of proximal annular end face 70 of abutment 44. In the preferred embodiment as shown, the axial length of splines 72 is about 1.0 mm, or 0.040 inch, and the recess distance "a" is a small fraction of that distance, preferably about 0.005 inch.

The splines and slots of the implant and abutment are complementarily shaped for inter-engagement. The splines 22 of the implant 10 are generally wedge-shaped in cross-section, as are the slots 82 of the abutment 44, whereas the splines 72 of the abutment are generally rectangular in cross-section, as are the slots 36 of the implant 10. By providing the generally wedge-shaped splines on the implant, and the generally rectangular-shaped splines on the abutment, a desirable hierarchy of failure is obtained. Because the wedge-shaped splines have a greater cross-sectional area than the rectangular splines in a plane perpendicular to the longitudinal axis, the wedge-shaped splines are less likely to fail in shear as torque is applied than are the rectangular-shaped splines. It is desirable that the abutment fail prior to the implant in response to excessive torque, as replacement of the abutment is a relatively simple matter compared to extracting and replacing the implant.

Figure 5:
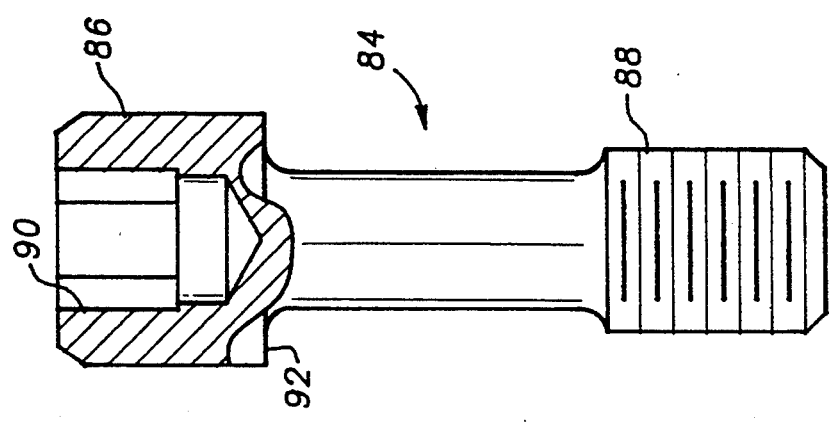
FIG. 5 is a side view, shown partially in section, of a screw useful for attaching the abutment of FIG. 3 to the implant of FIG. 1.

Referring to FIG. 5, there is illustrated a cap screw 84 having a head 86 at a distal end thereof and screw threads 88 at a proximal end thereof. Head 86 has a hexagonal recess 90 in the distal surface thereof for receipt of a driving tool (not shown), and an annular undersurface 92. The diameter of head 86 is slightly less than the diameter of cylindrical bore 58 of abutment 44 so as to be receivable therein, but greater than the diameter of cylindrical bore 66 of abutment 44 so that annular undersurface 92 engages annular shoulder 62 of abutment 44. The major diameter of screw threads 88 is slightly less than the diameter of cylindrical bore 66 so that screw threads 88 can pass therethrough and is nominally the same diameter d as the major diameter of threaded bore 40 of implant 10.

Figure 6:
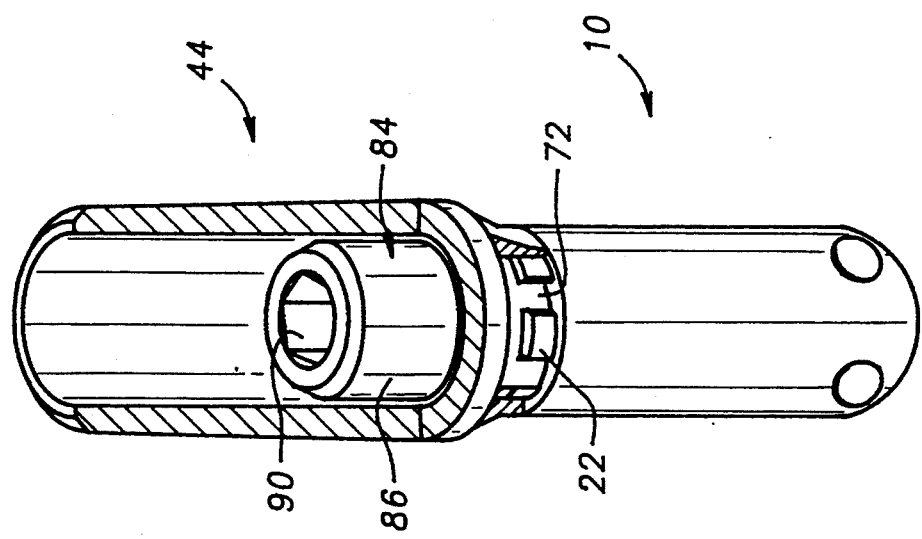
FIG. 6 is a perspective assembly view, shown partially in section, of the implant, abutment and screw of FIGS. 1-5.

After implant 10 has been implanted in the alveolar bone in accordance with well known surgical techniques and has become fixed therein by osseointegration, abutment 44 and screw 84 can be assembled thereto, as shown in FIG. 6. Typically, a hex driver tool is first engaged with hex recess 90 of screw 84 and the shank of screw 84 is inserted through cylindrical bores 58 and 66 of abutment 44 from distal end 48 such that screw threads 88 protrude proximally from proximal end 46 of abutment 44. Screw threads 88 are then started in threaded bore 40 of implant 10. Abutment 44 is then moved axially in the proximal direction toward implant 10 until proximal end 46 of abutment 44 engages distal end 16 of implant 10. Recess 68 of abutment 44 encounters chamfer 34 of implant splines 22 and is guided thereby such that splines 22 are piloted into recess 68. It is highly probable that the mating splines and slots of the implant and abutment will not be aligned to pass between one another at the initial approach of abutment 44 to implant 10. The likelihood is that splines 22 will be received into recess 68 only the distance "a", which in the preferred embodiment is about 0.005 inch, as the end faces 28 of splines 22 abut the end faces 76 of splines 72. The 0.005 inch engagement is sufficient to pilot abutment 44 relative to implant 10 so as to prevent relative lateral movement, but is not so great as to provide a tactile feedback that could be mistaken for full seating of the abutment 44 against the implant 10. The abutment can then be rotated about its longitudinal axis 60, which is now coaxial with the longitudinal axis 20 of implant 10, until splines 22 become aligned with slots 82, and splines 72 become aligned with slots 36 simultaneously, whereupon the splines of each member will abruptly drop into engagement with the respective mating slots of the other member, and the abutment 44 will suddenly be displaced approximately 0.040 inch in the proximal direction until annular end face 70 engages annular shoulder 18, at which point abutment 44 and implant 10 are fully engaged. Screw 84 can then be tightened in threaded bore 40 such that undersurface 92 engages annular shoulder 62 and draws abutment 44 tight against implant 10. It is significant that the initial amount of axial engagement between the abutment and implant for the purpose of piloting is a fraction of the total length of engagement incident upon full seating of the abutment on the implant. This assures that the initial piloting engagement is clearly distinguishable from full engagement by the tactile feedback provided. The piloting recess depth "a" should be less than one-half the total length of engagement of the splines, and preferably about one-eighth of the total length of engagement.

Figure 7:
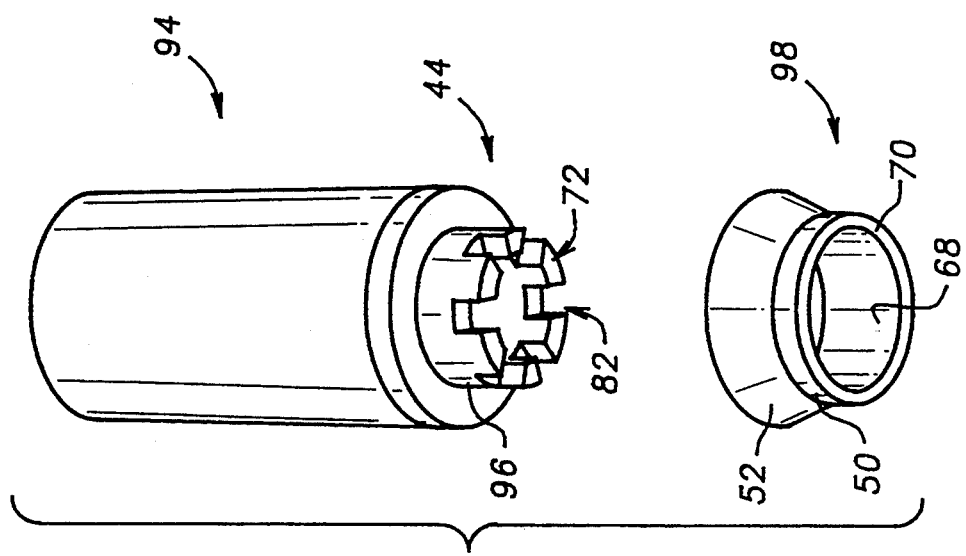
FIG. 7 is a perspective exploded view of the abutment of FIG. 3 showing a preferred method of construction.

Referring to FIG. 7, there is illustrated the preferred method of construction of the splines and slots of abutment 44. Because of the relative difficulty of machining recessed wedge-shaped slots, it is preferred to manufacture the abutment from two separate components. A first component 94 is preferably an integral piece having a raised cylinder 96 in which the generally wedge-shaped slots 82 have been machined, leaving the generally rectangular-shaped splines 72 therebetween, resulting in a castellated appearance. A second ring component 98 provides outer surface 50 and 52, annular end face 70, and recess 68. Ring component 98 is pressed onto castellated cylinder 96 in an interference fit relationship, resulting in the configuration illustrated above in FIGS. 3 and 4.

While the present invention has been illustrated and described with particularity in terms of a preferred embodiment, it should be understood that no limitation of the scope of the invention is intended thereby. The scope of the invention is defined only by the claims appended hereto. It should also be understood that variations of the particular embodiment described herein incorporating the principles of the present invention will occur to those of ordinary skill in the art and yet be within the scope of the appended claims.

What is claimed is:

1. A dental implant assembly comprising:
   an implant for osseointegration in alveolar bone, said implant including an elongate body having a proximate end and a distal end, an axial threaded bore open at said distal end, an annular shoulder at said distal end, and a plurality of splines spaced from one another to define slots therebetween and disposed circumferentially about the opening of said threaded bore at said distal end and extending axially away from said shoulder, each of said splines having a curved outer wall lying on a common circle disposed radially inwardly of said shoulder;
   an abutment removably attached to said implant for supporting a tooth prosthesis, said abutment including a proximal end and a distal end and an annular end face at said proximal end of said abutment in engagement with the annular shoulder of said implant, an axial bore having an internal shoulder, a cylindrical recess disposed radially inwardly of said annular end face and receiving said splines of said implant therewithin, said cylindrical recess communicating with said axial bore of said abutment, and a plurality of circumferentially spaced axially extending splines defining slots therebetween disposed within said cylindrical recess, each of said splines of said abutment being received in a respective slot of said implant between adjacent splines of said implant, and each of said slots of said abutment receiving a respective spline of said implant between adjacent splines of said abutment, the splines of said abutment having proximal end faces and having an axial length, the proximal end faces being recessed axially from said annular end face by an amount less than one half the axial length of said splines of said abutment; and
   a screw received in said axial bore of said abutment and having a head engaging said internal shoulder of said axial bore of said abutment and having screw threads threadedly engaged with the threaded bore of said implant.

2. The dental implant assembly of claim 1, in which said cylindrical recess of said abutment has an internal diameter and said common circle on which the outer walls of the splines of said implant lie has a diameter, the diameter of said cylindrical recess and the diameter of said common circle being nominally equal such the splines of said implant are received within the cylindrical recess in a relatively close-fitting piloting relationship.

3. The dental implant assembly of claim 1, in which said slots of said implant are diametrically opposed and have planar sidewalls that lie on each side of a line drawn diametrically across said implant.

4. The dental implant assembly of claim 1, in which said splines of said abutment are diametrically opposed and have planar sidewalls that lie on each side of a line drawn diametrically across said abutment.

5. The dental implant assembly of claim 1, in which the splines of said implant have side walls that tend toward convergence, and the splines of said abutment have side walls that are parallel, the splines of said implant having a greater cross-sectional area than the splines of said abutment.

6. The dental implant assembly of claim 1, in which the proximal end faces of the splines of the abutment are recessed axially from the annular end face of the abutment about 0.005 inch.

7. The dental implant assembly of claim 1, in which the proximal end faces of the splines of the abutment are recessed axially from the annular end face of the abutment by about one-eighth the axial length of said splines of said abutment.

8. An abutment for attachment to an implant for supporting a tooth prosthesis, said abutment including a proximal end and a distal end and an annular end face at said proximal end, an axial bore having an internal shoulder, a cylindrical recess disposed radially inwardly of said annular end face, said cylindrical recess communicating with said axial bore, and a plurality of circumferentially spaced axially extending splines defining slots therebetween disposed within said cylindrical recess, the splines of said abutment having proximal end faces and having an axial length, the proximal end faces being recessed axially from said annular end face by an amount less than one half the axial length of said splines of said abutment.

9. The abutment of claim 8, in which said splines of said abutment are diametrically opposed and have planar sidewalls that lie on each side of a line drawn diametrically across said abutment.

10. The abutment of claim 9, in which the slots of said abutment have side walls that tend toward convergence.

11. The abutment of claim 8, in which the proximal end faces of the splines of the abutment are recessed axially from the annular end face of the abutment about 0.005 inch.

12. The abutment of claim 8, in which the proximal end faces of the splines of the abutment are recessed axially from the annular end face of the abutment by about one-eighth the axial length of said splines of said abutment.

* * * * *

UNITED STATES PATENT AND TRADEMARK OFFICE
CERTIFICATE OF CORRECTION

PATENT NO. : 5,449,291
DATED : September 12, 1995
INVENTOR(S) : Jeffrey D. Lueschen, et al It is certified that error appears in the above-indentified patent and that said Letters Patent is hereby corrected as shown below:

The drawing sheet, consisting of Fig. 7, should be deleted to be replaced with the drawing sheet, consisting of Fig. 7, as shown on the attached page.

Signed and Sealed this

Second Day of January, 1996

*Attest:*

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,449,291

DATED : September 12, 1995

INVENTOR(S) : Jeffrey D. Lueschen and Brooks J. Story

It is certified that error appears in the above-identified patent and that said Letters Patent is hereby corrected as shown below:

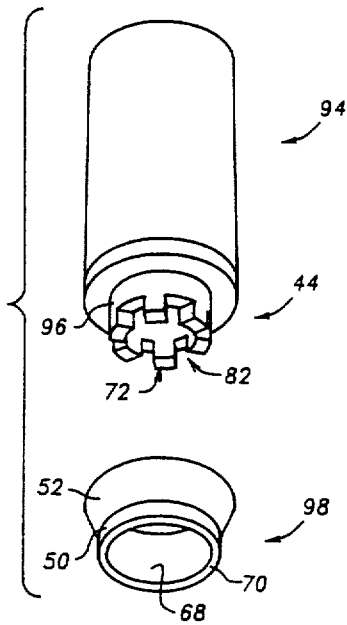

FIG. 7